(12) United States Patent
Mulzer et al.

(10) Patent No.: US 6,384,230 B1
(45) Date of Patent: May 7, 2002

(54) THIAZOLE DERIVATIVES, METHOD FOR THEIR PRODUCTION AND USE

(75) Inventors: Johann Mulzer; Anreas Mantoulidis, both of Vienna; Elisabeth Oehler, Klosterneuburg, all of (AT)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/462,882

(22) PCT Filed: Jul. 16, 1998

(86) PCT No.: PCT/EP98/04462

§ 371 Date: Jun. 14, 2000

§ 102(e) Date: Jun. 14, 2000

(87) PCT Pub. No.: WO99/03848

PCT Pub. Date: Jan. 28, 1999

(30) Foreign Application Priority Data

Jul. 16, 1997 (DE) .......................................... 197 31 316

(51) Int. Cl.[7] ............................................ C07D 277/22
(52) U.S. Cl. ........................................ 548/203; 548/204
(58) Field of Search .................................. 548/203, 204

(56) References Cited

FOREIGN PATENT DOCUMENTS

DE          19542986        5/1997

OTHER PUBLICATIONS

Dongfang Meng Et Al: "Studies toward a synthesis of epothilone A: Use of hydropyran templates for the management of acyclic stereochemical relationships" Journal of Organic Chemistry., Bd. 61, Nr. 23, 1996, Seiten 7998–7999, XP002035361 Easton US in der Anmeldung erwaehnt.

Johann Mulzer Et Al: "Synthesis of the C(11)–C(20) segment of the cytotoxic macrolide epothilone B" Tetrahedron Letters., Bd. 38, Nr. 44, 3. Nov. 1997, Seiten 7725–7728, XP002083207 Oxford GB.

Primary Examiner—Robert Gerstl
(74) Attorney, Agent, or Firm—Millen, White, Zelano & Branigan, P.C.

(57) ABSTRACT

Thiazole derivatives of formula II, in which $R^1$ means $C_1$–$C_4$ alkyl, $R^2$ means any protective group that can be chelated, $R^3$ means hydrogen or $C_1$–$C_4$ alkyl, Y means $CO_2R^4$, CHO, CH—$CH_2$ or $CH_2R^5$, whereby $R^4$ stands for $C_1$–$C_4$ alkyl and an optionally substituted benzyl group, $R^5$ stands for halogen, hydroxy, p-toluenesulfonate and —$OSO_2B$ and B stands for $C_1$–$C_4$ alkyl or $C_1$–$C_4$ perfluoroalkyl, can be produced free of diastereomers and are suitable for the production of epothilone A and epothilone B and derivatives thereof.

(II)

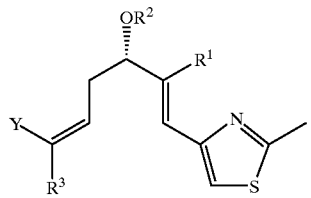

21 Claims, No Drawings

THIAZOLE DERIVATIVES, METHOD FOR THEIR PRODUCTION AND USE

The invention relates to the subject that is characterized in the claims, i.e., thiazole derivatives, process for their production and their use for the production of epothilone A, epothilone B or derivatives thereof.

It is known that the natural substances epothilone A (R=H) and epothilone B (R=methyl) (compound I, DE 195 42 986 A1, DE 41 38 042 C2)

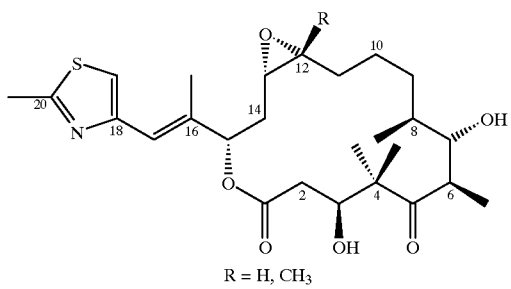

R = H, CH$_3$ have a fungicidal and cytotoxic action. According to references for an in vitro activity against breast and intestinal tumor cell lines, this compound class appears particularly advantageous for the formation of a pharmaceutical agent. Various working groups are therefore concerned with the synthesis of these macrocyclic compounds. The working groups start from different fragments of the macrocycle to synthesize the desired natural substances. Danishefsky et al. intends to synthesize from three fragments C(1)–C(2)+C(3)–C(9)+C(10)–C(20). The C(10)–C(20) fragment is a thiazole derivative, which could not be obtained free of diastereomers in a 15-stage synthesis (JOC, 1996, 61, 7998–7999). Freedom from diastereomers is often decisive, however, for the action and a requirement for the production of a pharmaceutical agent.

The object was therefore to prepare, in a manner free of diastereomers, suitable fragments, from which the macrocyclic compounds and derivatives thereof can be synthesized.

It was now found that the thiazole derivatives of formula II

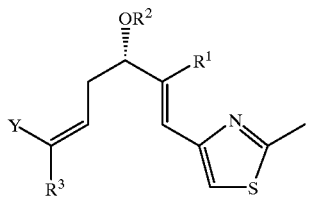

in which
 R$^1$ means C$_1$–C$_4$ alkyl,
 R$^2$ means any protective group that can be chelated,
 R$^3$ means hydrogen or C$_1$–C$_4$ alkyl,
 Y means CO$_2$R$^4$, CHO, CH=CH$_2$ or CH$_2$R$^5$,
  whereby
   R$^4$ stands for C$_1$–C$_4$ alkyl or an optionally substituted benzyl group,
   R$^5$ stands for halogen, hydroxy, p-toluenesulfonate or —OSO$_2$B and B stands for C$_1$–C$_4$ alkyl or C$_1$–C$_4$ perfluoroalkyl, can be produced free of diastereomers, and are suitable for the production of epothilone A and epothilone B and derivatives thereof.

C$_1$–C$_4$ alkyl for R$^1$, R$^3$, R$^4$ and B is defined as methyl, ethyl, propyl, isopropyl, butyl, isobutyl and tert-butyl.

Any protective group R$^2$ that can be chelated is defined as, for example, benzyl radicals such as, e.g., benzyl, p-methoxybenzyl (PMB), silyl radicals such as, e.g., trimethyl-silyl, 2-(trimethylsilyl)ethoxymethyl (SEM), tetrahydropyranyl, methoxymethyl, benzyloxymethoxymethyl, benzoyl, acetyl.

Substituted benzyl group R$^4$ can be, e.g., p-methoxybenzyl, 2,4-dimethoxybenzyl or a benzyl radical that is substituted by another electron-pushing substituent.

Halogen is defined as fluorine, chlorine, bromine and iodine, whereby bromine and iodine are preferred.

C$_1$–C$_4$ Perfluoroalkyl is defined as straight-chain or branched, completely fluorinated alkyl radicals, such as, for example, CF$_3$, C$_2$F$_5$, C$_3$F$_7$, C$_4$F$_9$.

Compounds II can be produced according to the process that is shown in diagram I, in which the synthesis is depicted by way of example for compound IIa with R$^2$=p-methoxybenzyl, R$^3$=methyl and Y=CO$_2$Et.

Starting from the naturally occurring (S)-malic acid (III), the α-hydroxy acid function with trifluoroacetic acid anhydride/methanol (a) is converted into the monomethylester. The acidic function that still remains is then reduced to alcohol with diborane in tetrahydrofuran (b). The (S)-(–)-methyl-2,4-dihydroxyester that is thus obtained is converted into the cyclic acetal (IV) with p-methoxybenzyldimethylacetal with camphersulfonic acid in toluene under reflux (c). The methylketone (V) is obtained from the methylester by reaction with one equivalent of methyllithium in 2 hours at –100° C. (d). Reaction with a C$_2$-, C$_3$- or C$_4$-organometallic compound, e.g., of a Grignard compound under common reaction conditions, results in the other radicals R$^1$. In the Wittig reaction (e), the 2-methyl-4-thiazolylmethyltriphenylphosphonium bromide, which is accessible in two stages from 1,3-dichloropropanone, is combined first with sodium hexamethyldisilazide at –78° C. in tetrahydrofuran before the ketone is added to it. After 1 hour and after heating to –40° C., the reaction results in an E/Z-mixture (E/Z=3.6:1). The E-isomer (VI) can be separated by simple flash chromatography. Regioselective release of the terminal hydroxy group by reductive opening of the acetal with 4 equivalents of diisobutylaluminum hydride in methylene chloride in 4 hours at –20° C. (f) produces a readily separable mixture (5.6:1 for the desired regioisomer) of the alcohol. After separation, the alcohol is converted into the corresponding aldehyde by Swern oxidation in one hour while being heated from –78° C. to 0° C. (g), and the aldehyde is reacted immediately to Wadsworth-Horner-Emmons condensation under Still's conditions (h) with ethyl-2-diethoxyphosphinylopropionate or the Horner reagent that is suitable corresponding to the desired radical R$^3$ with the addition of potassium hexamethyldisilazide, 18-crown-6 at –78° C. for one hour in tetrahydrofuran. An E/Z-mixture (E/Z=6.2:1) of the α,β-unsaturated ester is obtained, from which the Z-isomer (IIA) can be separated in a good yield. The use of the trifluoroethylphosphonate derivative results in a better selectivity of 15:1.

Diagram I

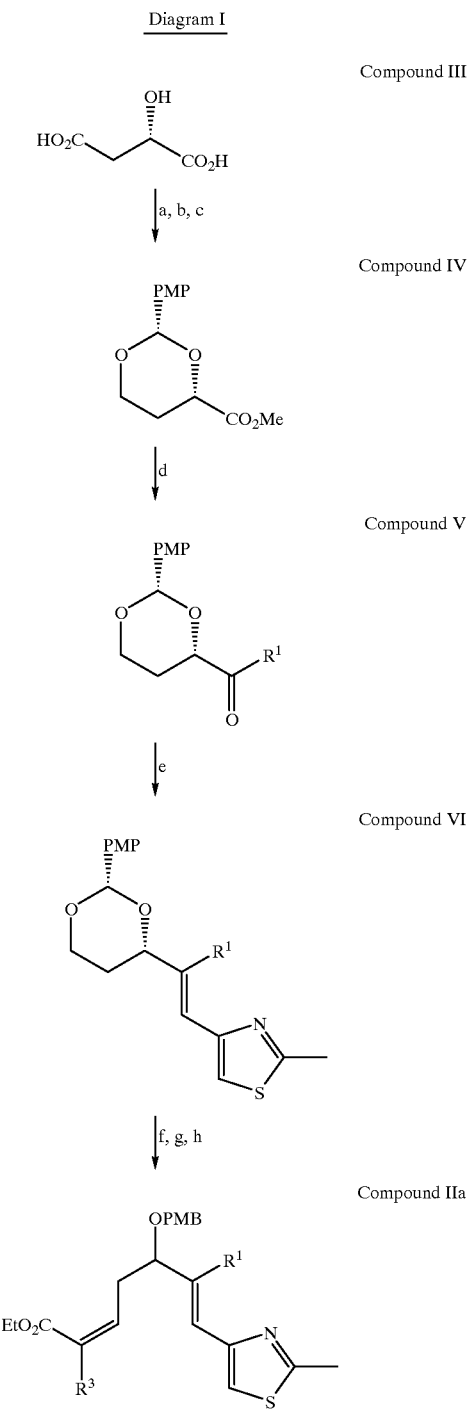

The compound of general formula IIa represents a central component of the synthesis of epothilone derivatives and epothilone itself.

The ester function in 11-position can be converted into any functionality that is required for the subsequent ring closure.

Derivatizations in 12- and 13-position (epothilone numbering system) are possible from the double bond. Thus, for example, conversion by Sharpless oxidation into the epoxide that is itself present in the epothilone:

In this respect, ester IIa is reduced with 3 equivalents of diisobutylaluminum hydride in tetrahydrofuran at −20° C. (i) into a α,β-unsaturated alcohol, and then the double bond of the allyl alcohol is epoxidated in a diastereo-selective manner with 4 Å molecular sieve, titanium tetraisopropylate, D-(−)-diisopropyltartrate, tert-butylhydroperoxide in methylene chloride for 3 hours at −30° C. (k).

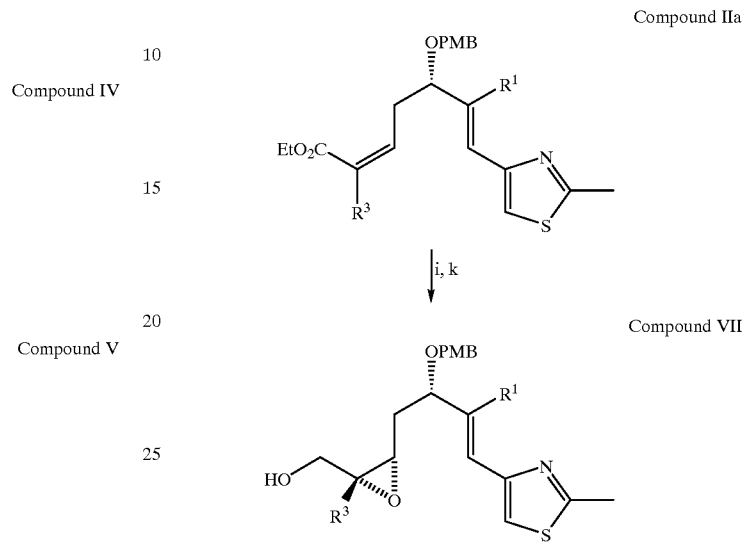

The hydroxy group in 15-position that is still present in protected form also allows derivatizations at this point or can be cleaved under conditions that are known in the literature.

Compounds with Y—CHO can be obtained by Dibal reduction of compound IIa in a way that is known in the literature.

Subsequent Wittig reaction results in compounds with Y=CH=CH$_2$.

The compounds with Y=CH$_2$R$^5$ with R$^5$=p-toluenesulfonate, (C$_1$–C$_4$)alkylsulfonate or (C$_1$–C$_4$) perfluoroalkylsulfonate can be obtained from alcohol (VII).

The compounds with Y=CH$_2$-halogen can be obtained from, e.g., the compound with Y=CH$_2$-p-toluenesulfonate or Y=OH in the usual way.

In contrast to the process of Danishefsky et al., only 10 stages are required for the synthesis up to the stage of the epoxide, and the thiazole derivative of formula IIa can be obtained free of diastereomers just like the epoxide. Another advantage consists in that the natural starting material that is used and the reactions of the synthesis allow larger amounts to be produced.

The further processing of the compounds according to the invention to epothilone A and B can be carried out as indicated in the reaction sequence below. The compound of general formula XI is further processed into epothilone B analogously to known processes by cleavage of the primary protective group, oxidation in 1-position, selective release of the 15-hydroxy group, as they are described by, for example, K. C. Nicolaou et al. In Nature, Vol.38-, 1997, pp. 268–272 and J. Am. Chem. Soc. 1997, 119, pp. 7960–7973:

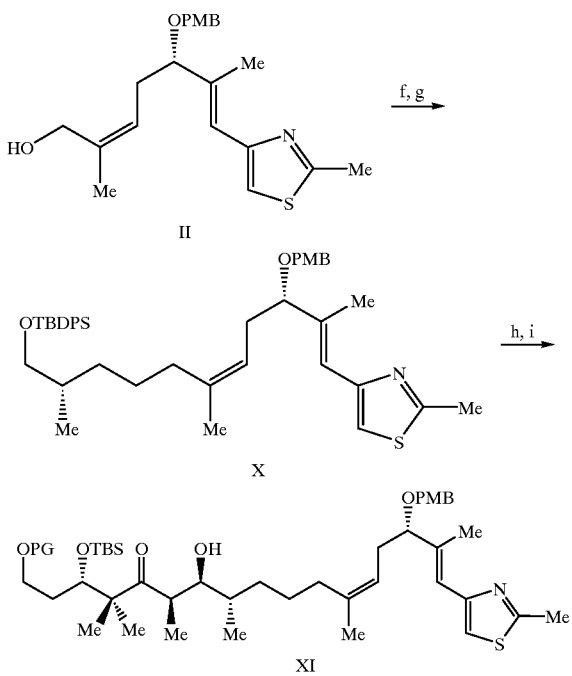

f) (i) iodide formation; (ii) sulfone coupling, 76.5%; g) desulfonation, 70%; h) desilylation, 98%; i) aldol reaction.

The examples below are used for a more detailed explanation of the subject of the invention, without intending that it be limited to these examples.

PREOPERATIVE METHODS

All reactions of organometallic reagents and all reactions in absolute solutions are performed in an environment that is devoid of air and moisture. Before the beginning of the test, the glass equipment that is used is heated several times in an oil pump vacuum and aerated with dry argon of the Linde Company. Unless otherwise indicated, all reaction batches are stirred magnetically.

Methylene chloride is dried on a basic aluminum oxide column of activity stage 1 (Woelm). After predrying on a basic aluminum oxide column over an 8:1 sodium/potassium alloy, diethyl ether is refluxed until the stable blue coloring of the benzophenone indicator is achieved and is freshly distilled off before use. Tetrahydrofuran (THF) is predried on KOH, filtered with a column that is coated with basic aluminum oxide and then distilled on potassium with triphenyl-methane as an indicator.

After predrying on calcium chloride, ethyl acetate (EE) is distilled off just like hexane (hex) before use for column chromatography in a rotary evaporator.

CHROMATOGRAPHIC PROCESS

All reactions are monitored by thin-layer chromatography (TLC) on silica gel-60-aluminum foils with the UV-indicator $F_{254}$ of the Merck Company. In most cases, solvent mixtures of hexane (hex) and ethyl acetate (EE) are used as mobile solvents. For visualization of non-UV-active substances, anisaldehyde glacial acetic acid/sulfuric acid (1:100:1) has been taken as a standard immersion reagent in most cases.

The preoperative column chromatography is performed on silica gel-60 of the Merck Company (0.04–0.063 mm, 230–400 mesh), whereby solvent mixtures of hexane (hex) and ethyl acetate (EE) or diisopropyl ether are used as eluant.

On an analytical scale as well as on a preoperative scale, the high-pressure liquid-chromatographic separations (HPLC) are performed on the module systems of the Knauer Company (pump 64, UV and RI detectors, columns and recorders), Waters/Millipore Company (Injection system U6K9) and Milton-Roy Company (integrator CI-10). For the analytical HPLC, in most cases a Knauer column (4,250 mm) with 5 μm Nucleosil is used, and for preoperative HPLC, a column (16,250 mm, 32,250 mm or 64,300 mm) with 7 μm or 5 μm of Nucleosil 50 is used.

COLOR REAGENTS

Color reagent I (F I): In the case of most compounds that can be reduced, 1 g of cerium(IV) sulfate in 10 ml of concentrated sulfuric acid and 90 ml of water produce an intensive blue color reaction during drying.

Color reagent II (F II): A 10% ethanolic solution of molybdatophosphoric acid represents another immersion reagent for detecting unsaturated and reducible compounds. In contrast to color reagent I, the molybdate-color reagent, especially pertaining to several functionalities, shows a broader color spectrum in virtually identical reliability.

Color reagent III (F III): 1 ml of anisaldehyde in 100 ml of ethanol and 2 ml of concentrated sulfuric acid represent an extremely sensitive color reagent that also likely shows the broadest color spectrum.

Color reagent IV (F IV): The vanillin immersion bath reagent is sensitive much like the anisaldehyde color reagent and like the latter shows an almost broad color spectrum.

Color reagent V (F V): 1 g of 2,4-dinitrophenylhydrazine in 25 ml of ethanol, 8 ml of water and 5 ml of concentrated sulfuric acid represent an excellent immersion reagent that responds selectively to aldehydes even without being heated and that responds somewhat more slowly to ketones.

Color reagent VI (F VI): A 0.5% aqueous solution of potassium permanganate indicates groups that can be oxidized by decolorization, whereby unsaturated, non-aromatic structural units react spontaneously without heating.

SPECTROSCOPIC PROCESS AND GENERAL ANALYSIS

NMR-Spectroscopy

The $^1$H-NMR spectra are recorded with an AC 250, AM 270 or AMX 500 spectrometer of the Bruker Company with the substances as a solution in deuterated solvents and tetramethylsilane as an internal standard. The evaluation of the spectra is carried out according to rules of the first order. If a signal multiplicity that occurs cannot be explained in this way, the indication of the observed line assembly is done. To determine the stereochemistry, the NOE spectroscopy (Nuclear Overhauser Effect) is used.

To characterize the signals, the following abbreviations are used: s (singlet), d (doublet), dd (double doublet), ddd (6-line system with two identical coupling constants or an 8-line system with three different coupling constants), t (triplet), q (quartet), quint (quintet), sext (sextet), sept (septet), m (multiplet), mc (centered multiplet), br (broad) and v (masked signal).

The $^{13}$C-NMR spectra are measured with an AC 250 of the Bruker Company with $CDCl_3$-signals at 77.0 ppm as an internal standard, whereby the portion resonances are broadband-decoupled.

ABBREVIATIONS THAT ARE USED abs.: absolute, Ar: aryl/aromatic compound, ber.: calculated, Brine: cold saturated common salt solution, c:

concentration, COSY: correlated spectroscopy, DC: thin-layer chromatography, DDQ: dichloro-dicyano-quinone, d.e.: excess diastereomerism, DIBAL: diisobutyl-aluminum hydride, DMF: N,N'-dimethylformamide, DMS: dimethyl sulfide, DMSO: dimethyl sulfoxide, ds: diastereoselection, EA: elementary analysis, e.e.: enantiomeric excess, EE: ethyl acetate, EI: electron impact ionization, eq: equivalent (s), eV: electron volt, FG: functional group, gef.: found, ges.: saturated, h: hour(s), hex: n-hexane, HMDS: hexamethyldisilazide, HPLC: high-pressure liquid chromatography, Hünig Base: N-ethyl-diisopropylamine, HRMS: high-resolution mass spectrometry, HV: high vacuum, iPrOH: 2-propanol, IR: infrared spectrometry/infrared spectrum, J: coupling constant, LDA: lithium diisopropylamine, Lsg.: solution, Lsm.: solvent, Me: methyl, MeLi: methyllithium, min: minute(s), MS: mass spectrometry/mass spectra, NMR: nuclear-magnetic resonance, NOE: Nuclear Overhauser Effect, PCC: pyridinium chlorochromate, PG: protective group, Ph: phenyl, ppm: parts per million, Rkt.: reaction, rt: retention time, RT: room temperature (20–30° C.), Std.: hour(s), TBAF: tetra-n-butylammonium fluoride, TBDPS: tert-butyldiphenylsilyl-, TBS: tert-butyldimethylsilyl-, tert./t: tertiary, TFA: trifluoroethanoic acid, TFAA: trifluoroethanoic acid anhydride, TFMS: trifluoromethanesulfonic acid, THF: tetrahydrofuran, TMS: trimethylsilyl, u: g mol$^{-1}$.

EXAMPLE 1

(2S,4S)-2-[4-Methoxyphenyl]-1,3-dioxane-4-carboxylic Acid Methyl Ester

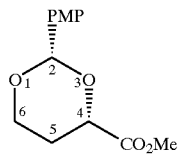

A W-5-2 $C_{13}H_{16}O_5$

M=252.26 g/mol

C 61.9% H 6.4% O 31.7%

6.7 g (50 mmol) of (S)-malic acid is introduced at 0° C. under argon into a heated 250 ml three-necked lowenthal flask. While being stirred, 30 ml of trifluoroacetic acid anhydride is very slowly added via a dropping funnel (pressure equalization!). After the addition is completed, the ice bath is removed, and the reaction solution is stirred for 2 more hours at room temperature.

Trifluoroacetic acid and excess anhydride are now first removed in a water jet vacuum and then at the oil pump, and the crystalline residue is mixed drop by drop with 4.5 ml of methanol at 0° C. (pressure equalization, see above!) and stirred for about 12 hours after the ice bath is removed.

After concentration by evaporation and drying in a vacuum, the crystalline compound of (2S)-2-hydroxy-butane-1,4-dioic acid-1-monomethyl ester in 70 ml of absolute THF is dissolved and mixed drop by drop with 100 ml of a 1M borane-THF complex solution at 0° C. It is stirred for 3 more hours, and then the reaction is carefully halted by adding 60 ml of methanol drop by drop. After concentration by evaporation in a rotary evaporator, the viscous oil is mixed several times with methanol to remove trimethylborate and concentrated by evaporation in a vacuum. (The dihydroxy compound is optionally present in a mixture with hydroxy-butyrolactone; the crude product that is thus purified is immediately further reacted).

The above crude product in 220 ml of absolute toluene with 12.8 ml (65 mmol) of anisaldehyde dimethylacetal is introduced into a heated 250 ml three-necked lowenthal flask, mixed with 1.16 g of camphersulfonic acid and stirred under reflux for 5 hours on a Soxhlet extractor that is filled with activated 4 Å molecular sieve. After the solution is cooled, it is filtered with a frit that is coated with silica gel, rewashed with ether, shaken out with saturated sodium carbonate solution, dried on magnesium sulfate, filtered and concentrated by evaporation. The crude product is chromatographed on a 5:1-hex/EE-silica gel column. 6.65 g (52.7%) of the thermodynamic acetal product is obtained as a crystalline compound.

$^1$H-NMR (400 MRz, CDCl$_3$): δ in ppm=1.85 (dtd, $J_{3a,3b}$=13.5 Hz, $J_{3a,4a\ and\ 2}$≅2.8 Hz, $J_{3a,4b}$=1.5 Hz, 1H, 3a-H); 2.12 (dddd, $J_{3b,3a}$=13.5 Hz, $J_{3b,2}$≡$J_{3b,4a}$≡12.0 Hz, $J_{3b,4b}$=5.0 Hz, 1H, 3b-H); 3.76+3.77 (s, 3H+3H, OCH$_3$+CO$_2$CH$_3$); 3.98 (ddd, $J_{4a,3b}$≅$J_{4a4b}$≅12 Hz, $J_{4a,3a}$=2.5 Hz, 1H, 4a-H); 4.30 (ddd, $J_{4b,4a}$=12.0 Hz, $J_{4b,3b}$=5.0 Hz, $J_{4b,3a}$=1.5 Hz, 1H, 4b-H); 4.49 (dd, $J_{2,3b}$=12.0 Hz, $J_{2,3a}$=2.8 Hz, 1H, 2-H); 5.47 (s, 1H), OCHArO); 6.87 (dt, $J_{ArH,\ ArH}$=8.5 Hz, $J_{ArH,\ OCHArO}$=2.0 Hz, 2H, ArH); 7.42 (d, $J_{ArH,\ ArH}$=8.5 Hz, 2H, ArH). $^{13}$C-NMR (100 MHz, CDCl$_3$): δ in ppm=28.1 (C-3); 52.2 (C-6); 55.5 (C-11); 66.6 (C-4); 75.7 (C-2); 101.3 (C-5); 113.6 (C-9); 127.5 (C-8); 130.2 (C-7); 160.1 (C-10); 170.4 (C-1). IR (Si film); v in cm$^{-1}$=2961m; 2855m; 1730s; 1614m; 1519m; 1445m; 1375m; 1310s; 1251vs; 1207m; 1185m; 1137s; 1096s; 1070m; 1028vs; 993vs; 832s. MS (EI, 70 eV, 30° C.): m/e=252 (98) [M$^+$]; 251 (100) [M$^+$-H]; 221 (14); 193 (86); 169 (16); 137 (88); 136 (98); 135 (98); 121 (28); 119 (34); 109 (42); 77 (53); 69 (58); 57 (25); 55 (31). Melting point: 78–80° C. (from Et$_2$O); C$_{13}$H$_{16}$O$_5$: (M=252.26 g/mol$^{-1}$); EA: Cld: C: 61.90% H: 6.39%; Fnd: C: 61.67% H: 6.43%.

EXAMPLE 2

(2S,4S)-(2-[4-Methoxyphenyl]-1,3-dioxan-4-yl)-ethan-1-one

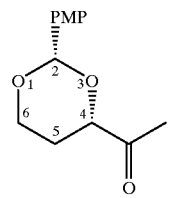

A W-6-2 $C_{13}H_{16}O_4$

M=236.26 g/mol

C 66.1% H 6.8% O 27.1%

In a 250 ml three-necked round-bottom flask, 2.066 g (8.19 mmol) of the compound that is obtained from Example 1 in about 80 ml of absolute THF is mixed drop by drop at –100° C. with 7.17 ml of a 1.6 M MeLi solution (1.4 equivalents), and it is stirred for 1–2 more hours.

In the case of complete conversion of the educt, the cooling bath is removed and quickly quenched with about 100 ml of saturated NH$_4$Cl solution and stirred for 1 more hour. For working-up, it is diluted with ether, the phases are separated, the organic phase is washed with water, saturated NaHCO$_3$ solution, water and brine, and the aqueous phase is extracted once more with ether. The combined organic phases are dried on magnesium sulfate, filtered and spun in, whereby the product is optionally already crystallized out (in this case, it can be washed once with cold hexane for purification). After chromatography on a 3:1-hex/EE-silica gel column, 1.656 g (85.6%) was obtained.

$^1$H-NMR (400 MHz, CDCl$_3$): δ in ppm=1.79 (dtd, J$_{2a,2b}$=13.3 Hz, J$_{2a,1a}$ and $_3$=2.9 Hz, J$_{2a,1b}$=1.5 Hz, 1H, 2a-H); 1.90 (dddd, J$_{2b,2a}$=13.3 Hz, J$_{2b,2}$ and $_3$=11.8 Hz, J$_{2b,1b}$=4.9 Hz, 1H, 2b-H); 2.27 (s, 3H, COCH$_3$); 3.79 (s, 3H, OCH$_3$); 3.96 (td, J$_{1a,1b}$≅J$_{1a,2b}$≅11.8 Hz, J$_{1a,2a}$=2.5 Hz 1H, 1a-H); 4.25 (dd, J$_{3,2b}$=11.3 Hz, J$_{3,2a}$=3.0 Hz, 1H, 3-H); 4.29 (ddd, J$_{1b,1a}$=11.3 Hz, J$_{1b,2b}$=4.9 Hz, J$_{1b,2a}$=1.0 Hz, 1H, 1b-H); 5.50 (s, 1H, OCHArO); 6.89 (d, J$_{ArH, ArH}$=8.8 Hz, 2H, ArH); 7.43 (d, J$_{ArH, ArH}$=8.4 Hz, 2H, ArH). $^{13}$C-NMR (100 MHz, CDCl$_3$): δ in ppm=25.7 (C-5); 27.2 (C-2); 55.2 (C-11); 66.7 (C-1); 81.5 (C-2); 100.9 (C-6); 113.6 (C-9); 127.3 (C-8); 130.5 (C-7); 160.1 (C-10); 208.1 (C-1). IR (Si film): v in cm$^{-1}$=2999m; 2969s; 2931s; 2909m; 2871s; 2832m; 1710s; 1615m; 1590m; 1520s; 1464m; 1452m; 1429s; 1399m; 1359vs; 1328w; 1310m; 1296m; 1236vs; 1220m; 1207m; 1180s; 1119s; 1100s; 1069m; 1035vs; 1018vs; 992vs; 971vs; 948m; 833vs. MS (EI, 70 eV, 30° C.): m/e=236 (88) [M$^+$]; 235 (91); 221 (20); 194 (72); 193 (78); 163 (33); 153 (27); 137 (88); 136 (88); 135 (86); 121 (77); 109 (85); 100 (28); 92 (47); 84 (99); 83 (65); 77 (92); 65 (31); 63 (31); 57 (43); 55 (31); 43 (100). Melting point: 74–76° C.; C$_{13}$H$_{16}$O$_4$: (M-236.26 g·mol$^{-1}$); EA: Cld: C: 66.09% H: 6.83%; Fnd: C: 66.34% H: 6.99%.

EXAMPLE 3
N (2'S,4'S,1E)-4-[2-(4-Methoxyphenyl-1,3-dioxan-4-yl)-prop-1-enyl]-2-methylthiazole

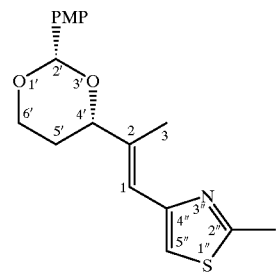

A M-5-2 C$_{18}$H$_{21}$NO$_3$S
M=331.42 g/mol
C 65.2% H 6.4% N 4.2% O 14.5% S 9.7%

In a 100 ml three-necked lowenthal flask, 1.475 g (3.25 mmol; 1.3 equivalent) of Wittig reagent (2-methyl-thiazol-4-yl-methyl-triphenylphosphonium bromide) is suspended after renewed drying in an oil pump vacuum with 5 ml of absolute THF. After the suspension is cooled to −78° C., it is deprotonated with a solution of 715 mg (3.9 mmol; 1.2 equivalents) of NaHMDS, dissolved in 5 ml of absolute THF, by slow addition, and it is stirred for 15 more minutes. 590 mg (2.5 mmol) of the compound that is obtained from Example 2 that is dried once more directly before use and dissolved in 5 ml of absolute THF is slowly added in drops at −78° C., stirred for 5 more minutes, and then the cooling bath is removed and allowed to heat to room temperature. After about 40 minutes, the reaction solution is heated in a water bath to 4–50° C. and stirred for 1 hour.

For working-up, it is quenched by adding saturated NH$_4$Cl solution, the phases are separated, the organic phase is dried on magnesium sulfate, filtered and spun in. After chromatography on a 6:5:1-CH$_2$Cl$_2$/hex/EE-silica gel column, 171 mg of Z-olefin and 614 mg of E-olefin are obtained.

The olefination products are thus obtained in a yield of 94.75% at a ratio of 1:3:6-Z:E-olefin.

$^1$H-NMR (400 MHz, CDCl$_3$) (E-olefin): δ in ppm=1.67 (dtd, J$_{2a,2b}$=13.3 Hz, J$_{2a,1a}$ and $_3$=2.5 Hz, J$_{2a,1b}$=1.5 Hz, 1H, 2a-H); 2.02 (mc, 1H, 2b-H); 2.10 (d, J$_{4,5}$=1.0 Hz, 1H, 4-H); 2.69 (s, 3H), TAr—CH$_3$); 3.78 (s, 3H, OCH$_3$); 4.02 (td, J$_{1a,1b}$≅J$_{1a,2b}$≡11.5 Hz, J$_{1a,2a}$=2.5 Hz, 1H, 1a-H); 4.29 (ddd, J$_{1b,1a}$=11.5 Hz, J$_{1b,2b}$=5.0 Hz, J$_{1b,2a}$=1.5 Hz, 1H, 1b-H); 4.34 (mc, 1H, 3-H); 5.56 (s, 1H, OCHArO); 6.63 (1, J$_{5,4}$≅1.0 Hz, 1H, 5-H); 6.88 (mc, 2H, Ar—H); 6.97 (s, 1H, TAr—H); 7.44 (mc, 2H, Ar—H). $^{13}$C-NMR (100 MHz, CDCl$_3$) (E-olefin): δ in ppm=15.1 (C-16); 19.2 (C-9); 30.2 (C-2); 55.3 (C-15); 67.1 (C-1); 81.7 (C-3); 101.1 (C-10); 113.5 (C-13); 115.7 (C-7); 118.9 (C-5); 127.5 (C-12); 131.3 (C-11); 139.1 (C-4); 152.8 (C-6); 159.9 (C-14); 164.4 (C-8). IR (Si film): v in cm$^{-1}$=3105w; 3057w; 2959m; 2925m; 2850m; 1658w; 1614s; 1517s; 1463m; 1442m; 1429m; 1394m; 1371m; 1302s; 1248vs; 1215w; 1172s; 1152w; 1118s; 1096s; 1062w; 1034s; 977w; 830m. MS (EI, 70 cV, 40° C.): m/e=331 (41) [M$^+$]; 279 (35); 247 (23); 231 (21); 195 (34); 178 (24); 167 (54); 164 (52); 149 (57); 140 (43); 139 (51); 136 (92); 135 (100); 119 (96); 97 (40); 94 (44); 91 (69); 77 (36); 69 (52); 57 (44); 55 (43); 43 (50). C$_{18}$H$_{21}$NO$_3$S: EA: Cld: C: 65.23% H: 6.39% N: 4.22%; (M-33.42 g·mol$^{-1}$); Fnd: C: 65.37% H: 6.41% N: 4.40%.

EXAMPLE 4
(3S,4E)-3-[(4-Methoxyphenyl)methoxy]-4-methyl-5-(2-methylthiazol-4-yl)pent-4-enol

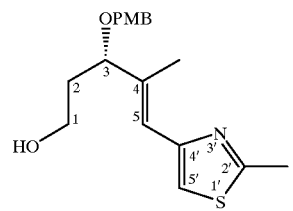

AM-12-2 C$_{18}$H$_{23}$NO$_3$S
M: 333.44 g·mol
C 64.8% H 7.0% N 4.2% O 14.4% S 9.6%

In 30 ml of absolute CH$_2$Cl$_2$, 662 mg (2 mmol) of the compound that is obtained from Example 3 is mixed drop by drop at −20° C. with 8 ml of a 1M DIBAL solution (4 equivalents) and stirred for about 5 hours. To halt the reaction, it is quenched with 1 ml of MeOH, and then saturated NaK-tartrate solution (30 ml) is slowly added. The solution is stirred overnight, whereby two clear phases have formed. The phases are separated, the aqueous phase is extracted twice with CH$_2$Cl$_2$, and the combined organic phases are washed with saturated NH$_4$Cl solution. After drying on MgSO$_4$, it is filtered and concentrated by evaporation in a vacuum.

Chromatography on a 2:1-hex/EE-silica gel column produced 594 mg (89.1%) of total yield at a 15:85 ratio ((89 mg); (505 mg)).

$^1$H-NMR (400 MHz, CDCl$_3$): δ in ppm=1.68 (dq, J$_{2a,2b}$=14.3 Hz, J$_{2a,1b}$ and $_3$=4.9 Hz, 1H, 2a-H); 1.94 (mc, 1H, 2b-H); 1.99 (s, 3H, 4-H); 2.37 (br s, 1H, 1-OH); 2.66 (s, 3H, TAr—CH$_3$); 3.68 (br mc, 2H, 1-H); 3.73 (s, 3H, OCH$_3$); 3.99 (dd, J$_{3,2a}$=8.9 Hz, J$_{3,2b}$=3.9 Hz, 1H, 3-H); 4.18+4.42 (d, J=11.3 Hz, 2H, OCH$_2$Ar each);. 6.48 (s, 1H, 5-H); 6.80 (mc, 2H, Ar—H); 6.93 (s, 1H, TAr—H); 7.18 (mc, 2H, Ar—H). $^{13}$C-NMR (100 MHz, CDCl$_3$): δ in ppm=13.6 (C-16); 19.2 (C-9); 36.7 (C-2); 55.2 (C-15); 61.1 (C-1); 69.9 (C-3); 84.3 (C-10); 113.9 (C-13); 115.9 (C-7); 121.1 (C-5); 129.4 (C-12); 130.2 (C-11); 139.1 (C-4); 152.6 (C-6); 159.2 (C-14): 164.7 (C-8). IR (Si film): v in cm$^{-1}$=3396br; 2926m; 2856w; 2835w; 1612m; 1586w; 1514vs; 1464m; 1453m;

1442m; 1302m; 1248vs; 1181m; 1173m; 1060m; 1035s; 821m. MS (EI, 70 eV, 40° C.): m/e=333 (9) [M⁺]; 281 (14); 231 (14); 212 (40); 197 (51); 164 (30); 135 (22); 122 (40); 121 (100); 113 (31); 97 (23); 91 (39); 77 (37); 69 (38). $C_{18}H_{23}NO_3S$: EA: Cld: C: 64.84% H: 6.95% N: 4.20%; (M=333.44 g·mol⁻¹); Fnd: C: 65.08% H: 7.00% N: 4.14%;

EXAMPLE 5
(5S,2Z,6E)-2,6-Dimethyl-5-[(4-ethoxyphenyl)-methoxy]-7-(2-methylthiazol-4-yl)hepta-2,6-dienoic Acid-ethyl Ester

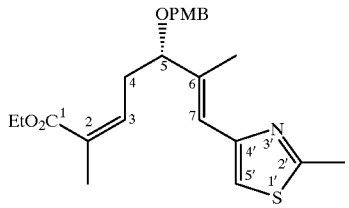

AM-14-1 $C_{23}H_{29}NO_4S$

M=415.54 g/mol

C 66.5% H 7.0% N 3.4% O 15.4% S 7.7%

In 30 ml of absolute $CH_2Cl_2$, 102 μl of oxalyl chloride (1.1 equivalents) is introduced, and after cooling to −78° C. under argon, it is slowly mixed with 187 μl of DMSO (2.5 equivalents) and stirred for 10 more minutes (cloudiness).

At −78° C., 354 mg (1.062 mmol) of the compound that is obtained from Example 4, dissolved in 5 ml of absolute $CH_2Cl_2$, is slowly added and stirred for 10 more minutes. Then, about 1 ml (>5 equivalents) of Hünig base is added, stirred for 15 more minutes, and then the cooling bath is removed. (Clear solution again). The reaction solution is diluted with 40 ml of a 1:1-hex/EE solution and quenched with ice water. The phases are separated, the aqueous phase is extracted twice more with ether, and the combined organic phases are dried on magnesium sulfate, filtered with a short silica gel frit, concentrated by evaporation in a vacuum, and dried at the oil pump. The raw aldehyde is used immediately for the subsequent reaction without further purification.

In 25 ml of absolute THF, 303.5 mg of 2-phosphonopropionic acid-triethyl ester (1.2 equivalents) and 842 mg of 18-crown-6-(3 equivalents) are introduced at −78° C. At this temperature, it is deprotonated by slowly adding 239 mg of KHMDS (1.15 equivalents), dissolved in about 5 ml of absolute THF, and it is stirred for 10 more minutes. Then, the raw aldehyde, dissolved in about 10 ml of absolute THF, is slowly added. After about 30 minutes, TLC monitoring indicated already complete conversion, so that the cooling bath was removed, and the reaction was quenched by adding saturated $NH_4Cl$ solution.

After phase separation, it is washed with saturated $NaHCO_3$ solution, the aqueous phases are extracted twice more with ether, and the combined organic phases are dried on magnesium sulfate. After the organic phases are filtered on short silica gel frits, it is concentrated by evaporation in a rotary evaporator. Chromatography on a 3:1 hex/EE silica gel precolumn produced 377 mg (85.46%) of isomer mixture at a ratio of about 6.2:1. To separate the double-bond isomers, chromatography on a 7:1-hex/EE-silica gel column or purification on the preoperative HPLC is recommended.

(In the meantime, the use of trifluoroethyl-phosphonate derivatives, which produced a selectivity of 15:1, was also studied.)

$^1$H-NMR (400 MHz, $CDCl_3$ (Z-isomer): δ in ppm=1.28 (t, J=7.5Hz, 3H, —$CO_2CH_2CH_3$); 1.88 (d, $J_{2,3}$=1.5 Hz, 3H, 2-H); 2.04 (d, $J_{6,7}$=1.0 Hz, 3H, 6-H); 2.73 (S, 3H), TAr—$CH_3$); 2.82 (mc, 2H, 4-H's); 3.80 (s, 3H, $OCH_3$); 3.88 (t, $J_{5,4a\ and\ 4b}$=7.0 Hz, 1H, 5-H); 4.17 (q, J=7.0 Hz, 2H, —$CO_2CH_2CH_3$); 4.24+4.49 (d, J=11.5 Hz, 2H, $OCH_2Ar$ each); 5.96 (tq, $J_{3,34a\ and\ 46}$=6.9 Hz, $J_{3,2}$=1.5 Hz, 1H, 3-H); 6.54 (s, 1H, 6-H); 6.87 (mc, 2H), Ar—H); 6.99 (s, 1H), TAr—H); 7.25 (mc, 2H, Ar—H). $^{13}$C-NMR (100 MHz, $CDCl_3$): δ in ppm=13.4 (C-20); 14.3 (C-13); 19.2 (C-11); 20.7 (C-21); 34.4 (C-4); 55.3 (C-19); 60.1 (C-12); 69.8 (C-14); 84.3 (C-5); 113.7 (C-17); 115.8 (C-9); 121.4 (C-7); 128.4 (C-2); 129.4 (C-16); 130.7 (C-15); 138.8 (C-3); 139.1 (C-6); 152.7 (C-8); 159.1 (C-18); 164.5 (C-10); 167.9 (C-1). MS (EI, 70 eV, 110° C.): m/e=415 (8) [M⁺]; 371 (13) [M⁻-OEt]; 294 (20); 289 (40); 288 (100); 248 (26); 231 (18); 204 (18); 164 (29); 138 (30); 122 (96); 121 (92); 113 (28); 97 (61); 91 (39): 78 (50); 77 (71); 69 (40); 53 (45); 43 (37). $C_{23}H_{29}NO_4S$: EA: Cld: C: 66.48% H: 7.03% N: 3.37%; (M-415.54 g·mol⁻¹); Fnd: C: 65.91% H: 6.77% N 3.29%.

EXAMPLE 6
(5S,2Z,6E)-2,6-Dimethyl-5-[(4-methoxyphenyl)methoxy]-7-(2-methyl-thia-zol-4-yl)hepta-2,6-dienol

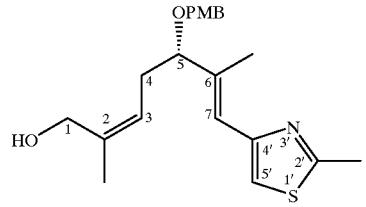

AM-15 $C_{21}H_{37}NO_3S$

M=373.51 g/mol

C 67.5% H 7.3% N 3.8% O 12.9% S 8.6%

417 mg (1.0035 mmol) of the compound that is obtained from Example 5 is introduced into 100 ml of absolute THF at −20° C., and then it is mixed drop by drop with 3 ml of a 1M DIBAL in heptane solution. After 3 hours, 1 more ml of DIBAL solution was added to complete the reaction conversion, and stirring was continued for 30 more minutes at −20° C.

To halt the reaction, it was quenched with 1 ml of MeOH, and after dilution with 50 ml of diethyl ether, 100 ml of semi-concentrated NaK-tartrate solution is added. After about 2–3 hours of vigorous stirring at room temperature, the phases are separated, the aqueous phase is extracted twice more with ether, and the combined organic phases are dried on magnesium sulfate, filtered and concentrated by evaporation in a vacuum. Chromatographic purification on a 1:1-hex/EE-silica gel column produced 272 mg (72.56%) of vinyl alcohol.

$^1$H-NMR (400 MHz, $CDCl_3$): δ in ppm=1.79 (s, 3H, 2-H); 2.03 (d, $J_{6,7}$=1.0 Hz, 3H, 6-H); 2.21 (mc, 1H, 4a-H); 2.47 (br, 1H, 1-OH); 2.52 (dt, $J_{4b,4a}$=14.3 Hz, $J_{4b,\ 3\ and\ 5}$=8.4 Hz, 1H, 4b-H); 2.70 (s, 3H), TAr—$CH_3$); 3.75 (dd, $J_{5,4a}$=8.4 Hz, $J_{5,4b}$=4.4 Hz, 1H, 5-H); 3.77 (s, 3H, $OCH_3$); 3.84+4.13 (br d, J=11.8 Hz, 2H, 1-H's each); 4.20+4.46 (d, J=11.3 Hz, 2H, $OCH_2AR$ each); 5.26 (t, $J_{3,4a\ and\ 4b}$=8.0 Hz, 1H, 3-H); 6.49 (s, 1H, 7-H); 6.84 (mc, 2H, Ar—H); 6.97 (s, 1H, TAr—H); 7.20 (mc, 2H, Ar—H). $^{13}$C-NMR (100 MHz, $CDCl_3$): δ in ppm=13.8 (C-18); 19.2 (C-11); 22.2 (C-19); 34.0 (C-4); 55.2 (C-17); 61.3 (C-1); 70.0 (C-12); 83.7 (C-5); 113.7 (C-15); 115.8 (C-9); 121.1 (C-7); 123.8 (C-3); 129.6 (C-14); 129.9 (C-13); 138.2 (C-2); 139.4 (C-6); 152.6 (C-8); 159.2 (C-16); 164.- (C-10). MS (EI, 70 eV, 50° C.): m/e=373 (9) [M⁺]; 357

(8); 307 (11); 289 (27); 288 (96); 219 (19); 197 (17); 167 (39); 164 (28); 149 (33); 138 (41); 122 (100); 121 (92); 119 (34): 109 (27); 97 (52); 91 (81); 78 (39); 77 (56) 69 (36); 43 (56).

EXAMPLE 7

(5S,2Z,6E)-2,6-Dimethyl-2,3-epoxy-5-[(4-methoxyphenyl)-methoxy]-7-(2-methylthiazol-4-yl)hept-6-enol

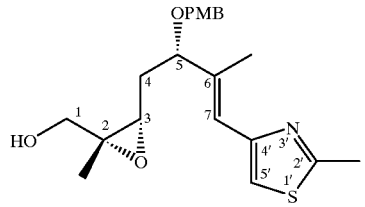

AM-16 $C_{21}H_{27}NO_4S$

M=389.50 g/mol

C 64.8% H 7.0% N 3.6% O 16.4% S 8.2%

20.5 mg (0.0874 mmol) of D-(−)-diisopropyl-tartrate and 21.7 μl (7.28 μmol) of titanium isopropoxide are added to a suspension of about 80 mg of activated, crushed 3 Å molecular sieve in 2 ml of absolute $CH_2Cl_2$ at −15° C.

199 μl of an approximately 5.5M tert-butyl-hydroperoxide solution in nonane is slowly added in drops at −30° C., and stirring is continued for 10 minutes. Then, the resulting reagent solution is mixed drop by drop at −30° C. with 265 mg (0.7095 mmol) of the compound that is obtained from Example 5, dissolved in about 1 ml of absolute $CH_2Cl_2$, and it is stirred for 3 days.

For working-up the reaction, it is first diluted with 15 ml of $CH_2Cl_2$, 1 ml of water is added, and stirring is continued for 30 minutes. Then, 1 ml (of brine/3N NaOH=1:1) is added, and stirring is again continued vigorously for 30 minutes. After phase separation, two extractions of the aqueous phase with $CH_2Cl_2$, drying of the combined organic phases on magnesium sulfate and filtration with a short Celite frit, it is concentrated by evaporation in a vacuum. Chromatography on a 1:1-hex/EE-silica gel column produced 235 mg (215 mg directly and 20 mg of ex $^{13}C$-data in the mixed fraction) (85.04%) and also 40 mg of the mixed radical.

$^1$H-NMR (400 MHz, $CDCl_3$): δ in ppm=1.40 (s, 3H, 2-H); 1.76 (ddd, $^2J_{4a,4b}$=15.3 Hz, $J_{4a,5}$=10.8 Hz, $J_{4a,3}$=9.9 Hz, 1H, 4a-H); 2.01 (ddd, $^2J_{4b,4a}$=14.8 Hz, $J_{4b,3}$=3.4 Hz, $J_{4b,5}$=2.5 Hz, 1H, 4b-H); 2.04 (d, $^4J_{6,7}$=1.0 Hz, 3H, 6-H); 2.71 (s, 3H, TAr—$CH_3$); 2.76 (dd, $J_{3,4a}$=9.9 Hz, $J_{3,4b}$=3.5 Hz, 1H, 3-H); 3.29 (dd, $J_{1-OH,1}$=10.8 Hz, $J_{1-OH,1}$=2.0 Hz, 1H, 1-OH); 3.45 (dd, $^2J_{1a,1b}$=11.8 Hz, $J_{1a,1-OH}$=2.0 Hz, 1H, 1a-H); 3.61 (t br, $^2J_{1b,1a}$=11.3 Hz, 1H 1b-H); 3.78 (s, 3H, $OCH_3$); 3.99 (dd, $J_{5,4a}$=10.8 Hz, $J_{5,4b}$=2.5 Hz, 1H, 5-H); 4.22+4.51 (d, $^2J$=11.5 Hz, 2H, $OCH_2Ar$ each); 6.49 (d, $^4J$=1.0 Hz, 1H, 7-H); 6.86 (mc, 2H, Ar—H); 7.00 (s, 1H, TAr—H); 7.22 (mc, 2H, Ar—H). $^{13}C$-NMR (100 MHz, $CDCl_3$): δ in ppm=13.4 (C-18); 19.2 (C-11); 20.4 (C-19); 33.7 (C-4); 55.2 (C-17); 60.5 (C-1); 62.1 (C-3); 64.2 (C-2); 70.0 (C-12); 81.3 (C-5); 113.9 (C-15); 116.4 (C-9); 121.7 (C-7); 129.0 (C-14); 131.1 (C-13); 138.1 (C-6); 152.3 (C-8); 159.5 (C-16); 164.9 (C-10).

What is claimed is:

1. A compound of formula II

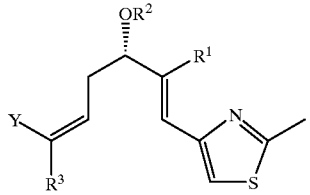

(II)

wherein $R^1$ is $C_1$–$C_4$ alkyl, $R^2$ is benzyl, p-methoxybenzyl (PMB), trimethyl-silyl, 2-(trimethylsilyl)ethoxymethyl (SEM), tetrahydropyranyl, methoxymethyl, benzyloxymethoxymethyl, benzoyl, or acetyl, $R^3$ is hydrogen or $C_1$–$C_4$ alkyl, Y is $CO_2R^4$, CHO, CH=$CH_2$ or $CH_2R^5$, $R^4$ is $C_1$–$C_4$ alkyl or an optionally substituted benzyl group, $R^5$ is halogen, hydroxy, p-toluenesulfonate or —$OSO_2B$, and B is $C_1$–$C_4$ alkyl or $C_1$–$C_4$ perfluoroalkyl.

2. A compound according to claim 1, wherein $R^1$ is $C_1$–$C_4$ alkyl, $R^2$ is p-methoxybenzyl, $R^3$ is methyl, Y is $CO_2R^4$, and $R^4$ is $C_1$–$C_4$ alkyl.

3. A compound according to claim 1, wherein $R^1$ is $C_1$–$C_4$ alkyl, $R^2$ is p-methoxybenzyl, $R^3$ is hydrogen or $C_1$–$C_4$ alkyl, and Y is $CO_2$-ethyl.

4. A compound of formula VII

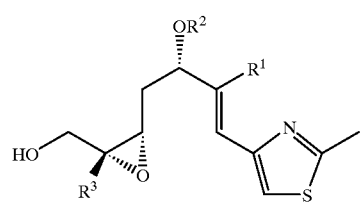

(VII)

wherein $R^1$ is hydrogen or $C_1$–$C_4$ alkyl, $R^2$ is benzyl, p-methoxybenzyl (PMB), trimethyl-silyl-2-(trimethylsilyl)ethoxymethyl (SEM), tetrahydropyranyl, methoxymethyl, benzyloxymethoxymethyl, benzoyl, or acetyl, and $R^3$ is hydrogen or $C_1$–$C_4$ alkyl.

5. A compound of formula VII according to claim 4 wherein $R^1$ is hydrogen or $C_1$–$C_4$ alkyl, $R^2$ is p-methoxybenzyl, and $R^3$ is hydrogen or $C_1$–$C_4$ alkyl.

6. A compound according to claim 1, wherein $R^4$ is $C_{1-4}$ alkyl or a benzyl radical which is substituted by an electron-donating substituent.

7. A compound according to claim 1, wherein $R^4$ is $C_{1-4}$ alkyl, p-methoxybenzyl or 2,4-dimethoxybenzyl.

8. A compound according to claim 1, wherein $R^5$ is bromine or iodine.

9. A compound according to claim 1, wherein $R^1$ is $CH_3$.

10. A compound according to claim 1, wherein $R^3$ is $CH_3$.

11. A compound according to claim 1, wherein $R^2$ is p-methoxybenzyl (PMB).

12. A compound according to claim 1, wherein Y is $COOR^4$.

13. A compound according to claim 1, wherein Y is $CO_2$-Ethyl.

14. A compound according to claim 1, wherein Y is $CH_2R^5$.

15. A compound according to claim 4, wherein $R^3$ is $CH_3$.

16. A compound according to claim 4, wherein $R^2$ is p-methoxybenzyl (PMB).

17. A compound according to claim 4, wherein $R^1$ is $CH_3$.

18. A compound according to claim 1, wherein said compound is (5S,2Z,6E)-2,6-Dimethyl-5-[(4-ethoxyphenyl)-methoxy]-7-(2-methylthiazol-4-yl)hepta-2,6-dienoic acid-ethyl ester.

19. A compound according to claim 1, wherein said compound is (5S,2Z,6E)-2,6-Dimethyl-5-[(4-methoxyphenyl)methoxy]-7-(2-methylthiazol-4-yl)hepta-2,6-dienol.

20. A compound according to claim 1, wherein said compound is (5S,2Z,6E)-2,6-Dimethyl-2,3-epoxy-5-[(4-methoxyphenyl)-methoxy]-7-(2-methylthiazol-4-yl)hept-6-enol.

21. A process for the preparation of a compound of formula IIa

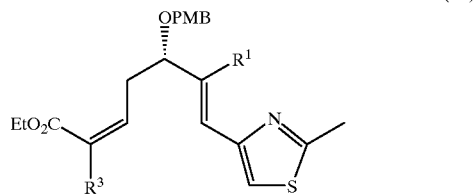

(IIa)

comprising:

converting the α-hydroxy acid function with trifluoroacetic acid/methanol of (s)-maleic acid (III) to methyl ester, reducing the still present acid function with diborane in tetrahydrofuran to alcohol, and converting the (S)-(−)-methyl-2,4-dihydroxyester that is obtained with p-methoxybenzyldimethylacetal to the cyclic acetal (IV),

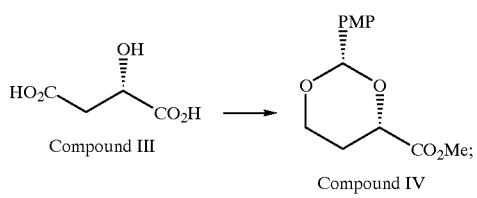

converting the methyl ester with a $C_1$–$C_4$ alkyl-organometallic compound to obtain the corresponding alkyl ketone (V),

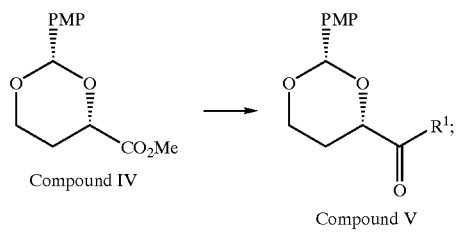

reacting the ($C_1$–$C_4$) alkyl ketone (V) in a Wittig reaction with the thiazolylphosphonium salt, and separating the E-isomer (VI),

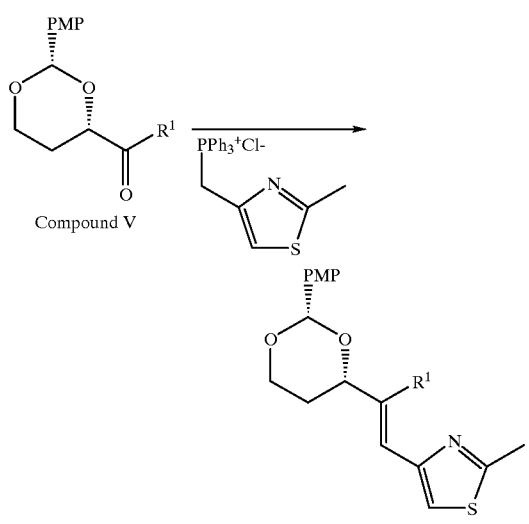

; and converting the E-isomer (VI) by reaction with diisobutylaluminum hydride, by Swern oxidation, by Wadsworth-Homer-Emmons condensation with ethyl-2-diethoxyphosphinylpropionate or by treatment with a Horner reagent that corresponds to $R^3$, and/or by purification of E-isomers to the Z-α, β-unsaturated ester (IIa),

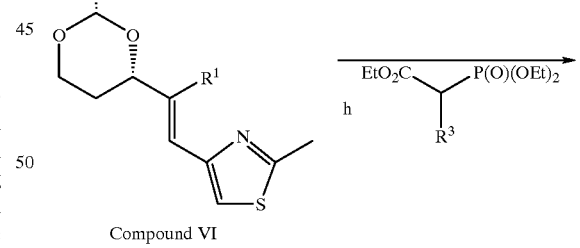

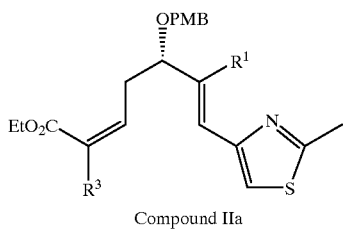

wherein
PMP is p-methoxyphenyl, and
PMB is p-methoxybenzyl.

* * * * *